(12) United States Patent
Medina

(10) Patent No.: US 9,744,075 B2
(45) Date of Patent: Aug. 29, 2017

(54) INSTRUMENT AND METHOD FOR CREATING A CONTROLLED CAPSULORHEXIS FOR CATARACT SURGERY

(71) Applicant: Rafael Medina, Williamsville, NY (US)

(72) Inventor: Rafael Medina, Williamsville, NY (US)

(*) Notice: Subject to any disclaimer, the term of this patent is extended or adjusted under 35 U.S.C. 154(b) by 0 days.

(21) Appl. No.: 15/012,253

(22) Filed: Feb. 1, 2016

(65) Prior Publication Data

US 2016/0143779 A1    May 26, 2016

Related U.S. Application Data

(62) Division of application No. 12/766,688, filed on Apr. 23, 2010, now Pat. No. 9,254,223.

(60) Provisional application No. 61/171,973, filed on Apr. 23, 2009.

(51) Int. Cl.
*A61F 9/007* (2006.01)
*A61B 17/32* (2006.01)

(52) U.S. Cl.
CPC  *A61F 9/00754* (2013.01); *A61B 2017/32006* (2013.01)

(58) Field of Classification Search
CPC ............... A61B 2017/32006; A61F 9/00754
See application file for complete search history.

(56) References Cited

U.S. PATENT DOCUMENTS

| 4,349,058 A | 9/1982 | Comparetto |
| 4,367,744 A | 1/1983 | Sole |
| 4,706,669 A | 11/1987 | Schlegel |
| 5,269,787 A * | 12/1993 | Cozean, Jr. .... A61B 17/320068 604/22 |
| 5,728,117 A * | 3/1998 | Lash ............... A61B 17/32053 606/107 |

(Continued)

FOREIGN PATENT DOCUMENTS

| CA | 2744036 A1 | 6/2010 |
| WO | 2006109290 A2 | 10/2006 |

OTHER PUBLICATIONS

PCT/US10/32273 International Search Report and Written Opinion mailed Dec. 15, 2010, 11 pages.

(Continued)

*Primary Examiner* — Julie A Szpira
(74) *Attorney, Agent, or Firm* — Lathrop & Gage LLP

(57) ABSTRACT

An instrument and method for creating a precise capsulorhexis as a step in cataract surgery is described. The instrument has a curvilinear cutting band attached to a longitudinal support component and cutting band extending on two sides of the support. In an embodiment, the cutting band has a sinusoidal shape. The support is coupled to a supporting structure, and then to a handle, the supporting structure is shaped to permit it to pass through an incision at a side of a cornea of the eye while positioning the cutting band on an anterior surface of an anterior capsule of a lens of the eye. In an embodiment of the method, the incision in the anterior capsule is formed by pressing the cutting band into the anterior capsule, and capsulorhexis is extended by tearing away the two tabs formed and defined by curvature of the cutting band.

13 Claims, 6 Drawing Sheets

(56) References Cited

U.S. PATENT DOCUMENTS

| | | | |
|---|---|---|---|
| 5,876,415 A * | 3/1999 | Pierce | A61F 9/013 606/166 |
| 6,165,190 A | 12/2000 | Nguyen | |
| 6,551,326 B1 * | 4/2003 | Van Heugten | A61F 9/00754 606/113 |
| 6,629,980 B1 * | 10/2003 | Eibschitz-Tsimhoni | A61F 9/0133 606/107 |
| 6,945,977 B2 | 9/2005 | Demarais et al. | |
| 7,374,566 B1 * | 5/2008 | Schossau | A61F 9/0133 606/107 |
| 8,137,344 B2 * | 3/2012 | Jia | A61B 18/14 606/45 |
| 9,254,223 B2 | 2/2016 | Medina | |
| 2004/0092982 A1 | 5/2004 | Sheffer | |
| 2010/0298820 A1 | 11/2010 | Ben-Nun | |
| 2010/0312232 A1 * | 12/2010 | Jia | A61B 18/10 606/29 |
| 2012/0035634 A1 * | 2/2012 | McGuckin, Jr. | A61B 17/320758 606/159 |
| 2012/0046680 A1 | 2/2012 | Dishler | |

OTHER PUBLICATIONS

Office Action corresponding to Canadian Patent Application No. 2,797,222, dated Apr. 4, 2016, 4 pages.

* cited by examiner

INSTRUMENT AND METHOD FOR CREATING A CONTROLLED CAPSULORHEXIS FOR CATARACT SURGERY

CROSS REFERENCE TO RELATED APPLICATIONS

This application is a division of U.S. application Ser. No. 12/766,688, filed Apr. 23, 2010, which claims priority from U.S. Provisional Patent Application Ser. No. 61/171,973, filed Apr. 23, 2009, both of which are incorporated herein by reference.

BACKGROUND

A cataract is a condition where the crystalline lens of an eye becomes cloudy or opaque enough to reduce vision. Cataract surgery today is a systematic process whereby an eye surgeon will disassemble the cataractous lens and remove and replace it with a synthetic prosthetic lens. Typically, the vision is restored without the need for thick spectacle correction.

The normal, natural, crystalline lens lies behind the iris of the eye and separates the anterior and posterior segments of the eye. The anterior chamber is normally filled with fluid called the aqueous humor. The cornea serves as the anterior boundary of the anterior chamber of the eye. The lens fills a thin membranous capsule that is supported radially by very fine hairlike fibers called zonules which in turn are supported by a smooth circular band of muscle called the cilliary body. The relaxation or contractile action of the cilliary body is thought to cause the expansion and contraction of the lens responsible for the natural lens's ability to dynamically alter its focal length during accommodation.

While early cataract surgeries involved removal of both the lens and its surrounding capsule, the current state of the art involves leaving most of the capsule intact so that the remaining capsule can support a synthetic prosthetic lens. In order to remove the lens from the capsule, an opening, or capsulotomy, must be made in the capsule. A capsulorhexis is an opening in the capsule having a particular smooth shape and particularly suitable for both removing the natural lens from the capsule and allowing insertion of a prosthetic lens into the residual capsule.

Most surgeons would argue that, outside of disassembling and removing the natural lens itself, the creation of a good capsulorhexis is probably the most important step in cataract surgery. The first step in performing a capsulorhexis entails puncturing the anterior capsule of the lens with a sharp needle like instrument or cystotome, creating an initial tear and a small capsular flap pedicle. Next, the flap of the initial tear is grasped with fine micro forceps. The surgeon then directs the tips of forceps to shear the anterior capsule in a clockwise or counterclockwise fashion thereby creating a quasi-circular opening in the anterior capsule of the lens. The current method requires the surgeon to grasp the edge of the capsular flap multiple times before completion. Depending on the anatomy of the patient's eye, this can take up to 5 or 10 minutes to complete. The aperture created in the anterior capsule is more often than not, imprecise in its diameter and irregular in its quasi-circular contour. Complications associated with this technique include poor control of capsulorhexis diameter, inadvertent propagation of capsular tear to the peripheral capsule and increased operative time.

SUMMARY

The disclosed subject matter presents a novel method and instrument useful for creating a repeatable, controlled capsulorhexis of desired size and shape. The instrument incorporates a serrated S shaped or reverse S shaped cutting surface, longitudinal and transverse structural support elements and a handle. In addition, the instrument can be used repeatedly after sterilization by high temperature autoclave thereby reducing costs associated with cataract surgery.

The purpose of the instrument is to create a capsulotomy with a precise incision boundary to facilitate a capsulorhexis during cataract surgery. The instrument is introduced into the anterior chamber of the eye after the initial incision is made and visco-elastic of appropriate viscosity fills the anterior chamber of the eye. The instrument is then centrally aligned over the anterior-posterior axis of the eye and made to gently puncture and incise the anterior capsule, thereby creating a precise reverse-S or S shaped capsulotomy.

The instrument has a curvilinear cutting band attached to a longitudinal support component and cutting band extending on two sides of the support. In an embodiment, the cutting band has elipsoidal shape. The support is coupled to a supporting structure, and thence to a handle. The supporting structure is shaped to permit it to pass through an incision at a side of a cornea of the eye while positioning the cutting band on an anterior surface of an anterior capsule of a lens of the eye. In an embodiment of the method, the incision in the anterior capsule is formed by gently pressing the cutting band into the anterior capsule. The complete capsulorhexis is created when the two tabs formed by incision created by the cutting band are grasped and gently sheared off in clockwise or counterclockwise circular arcs.

DETAILED DESCRIPTION OF THE EMBODIMENTS

Figure 1:
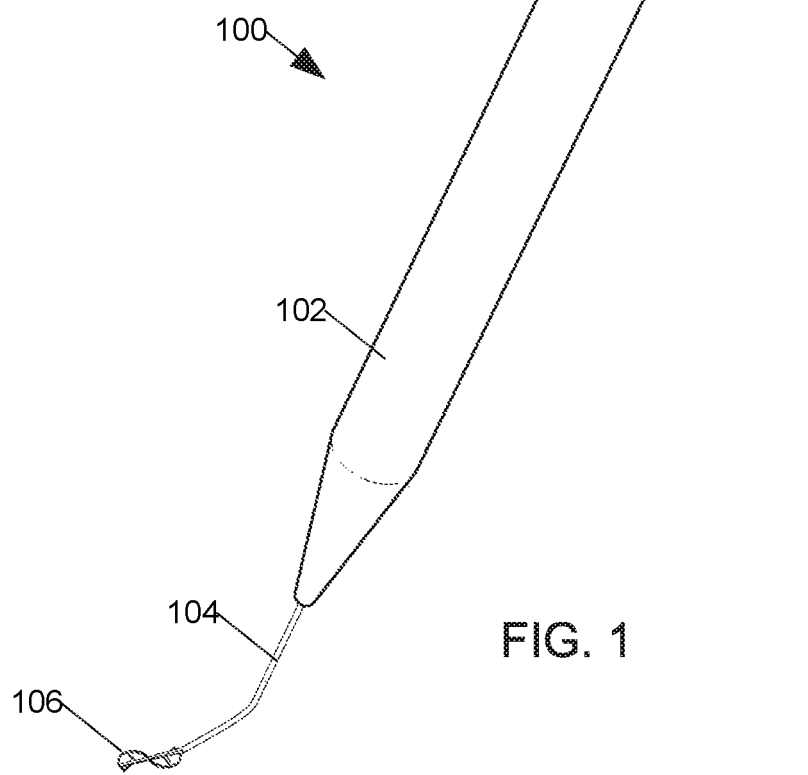
FIG. 1 is a view of the present instrument.

An instrument 100 for performing a capsulorhexis is illustrated in FIG. 1. The instrument has a handle 102, a support structure 104, and a cutting head 106; the cutting head is illustrated in FIGS. 3 and 4 as described below.

Figure 2:
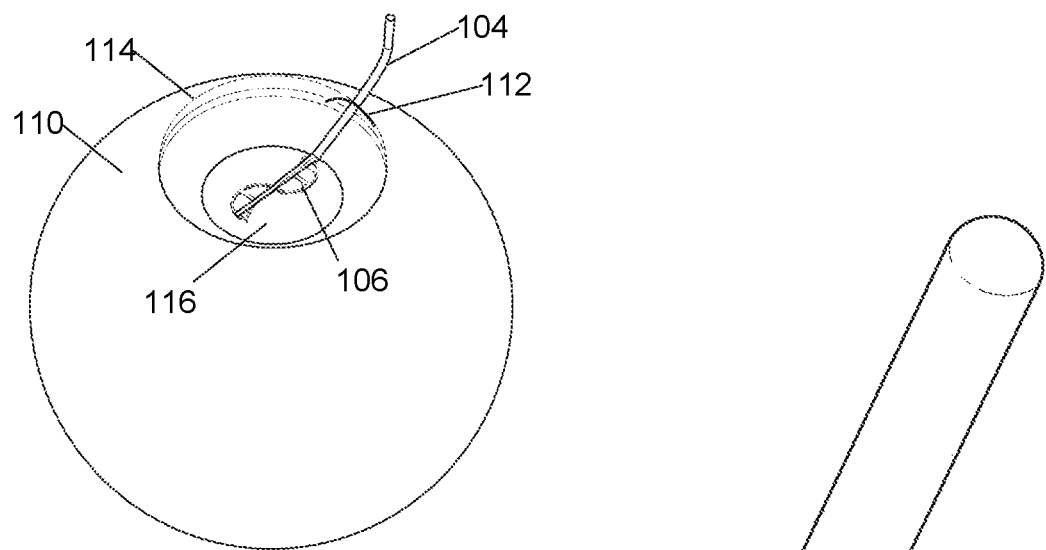
FIG. 2 is a perspective view illustrating the present instrument with its distal end placed in the anterior chamber of, and aligned over the axial centerline of, a model eye.

The instrument 100 is intended to be used to cut a precise reverse-S shaped, or in an alternative embodiment an S shaped, curvilinear pattern into the anterior capsule of the crystalline lens of an eye 110 for capsulorhexis during cataract surgery, as illustrated in FIG. 2. In use, the cutting head 106 is inserted by a surgeon through an incision 112 in eye 110, into the anterior chamber of the eye. The anterior chamber of the eye is the fluid-filled space lying beneath the cornea 114 of the eye 110, and above the crystalline lens 116. The cutting head 106 is centered over an anterior surface of the capsule of the crystalline lens 116 of eye 110. The cutting head 106 is then gently pressed into the lens to create a precisely shaped incision in the anterior surface of the capsule of the lens 116 of eye 110.

Figure 3:
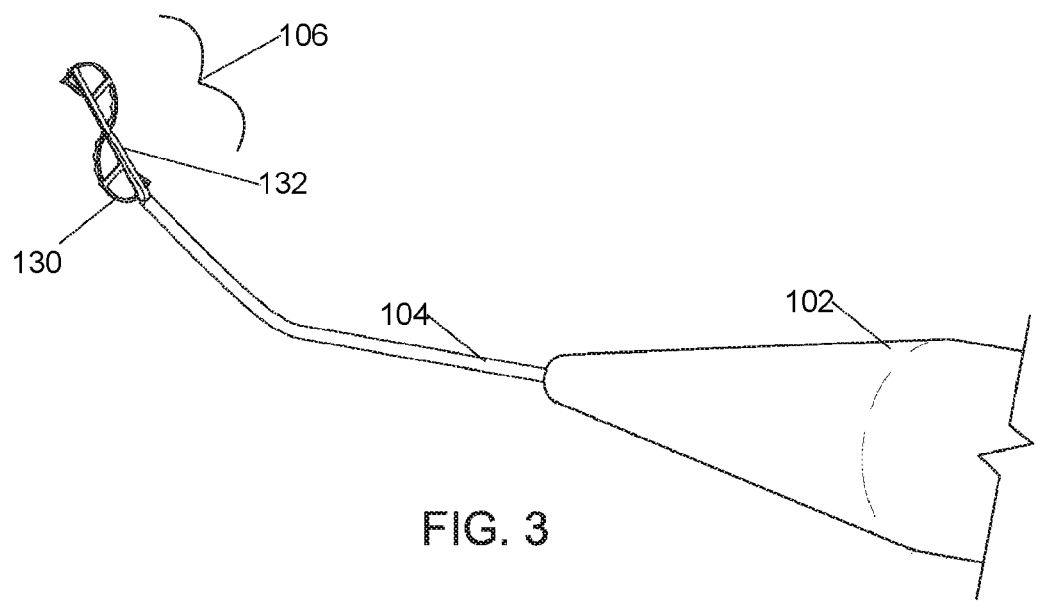
FIG. 3 is a view of the distal end of the instrument
Figure 4:
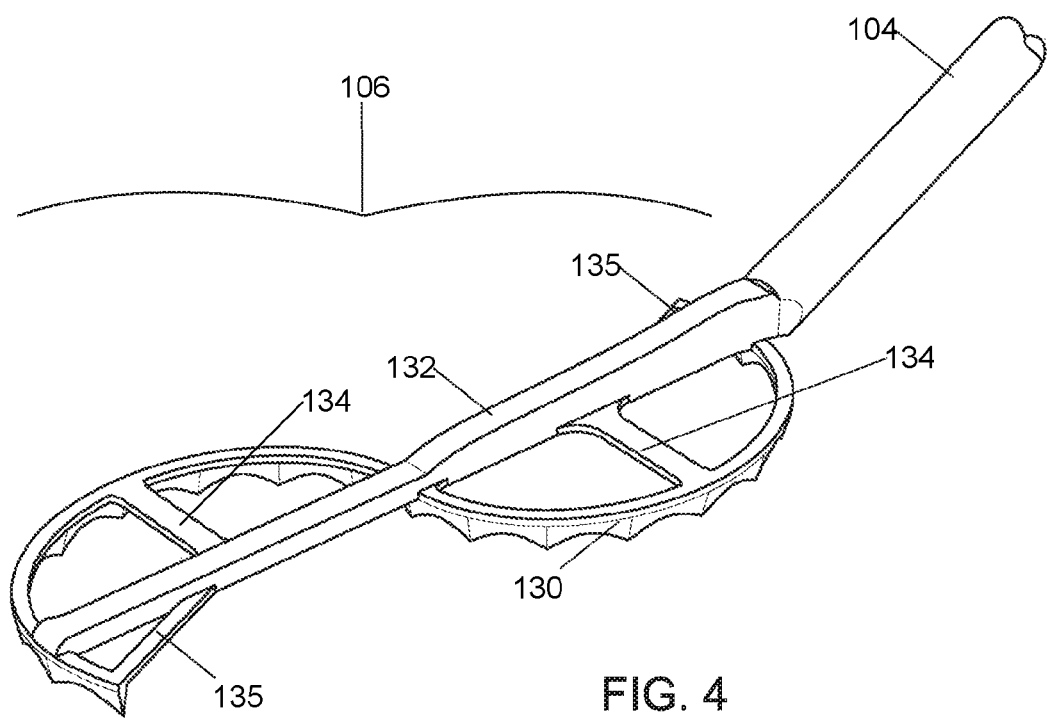
FIG. 4 is a view of the cutting head of the instrument

The distal end of the instrument, with cutting head 106, is shown in more detail in FIG. 3 and FIG. 4. Cutting head 106 includes a curved cutting band 130 with a serrated cutting edge, a structural support element having longitudinal 132 and transverse components 134 to support the cutting band 130. In an embodiment, cutting band 130 is made of a sharpened surgical stainless steel, and is welded to the longitudinal 132 and transverse 134 components of the support element. In an embodiment as illustrated, cutting band 130 is attached to longitudinal component 132 at three points, and has portions extending to both sides of longitudinal component 132. Additional angled support components 135 may be provided to anchor the ends or other points along the cutting band 130 to longitudinal component 132.

Figure 5:
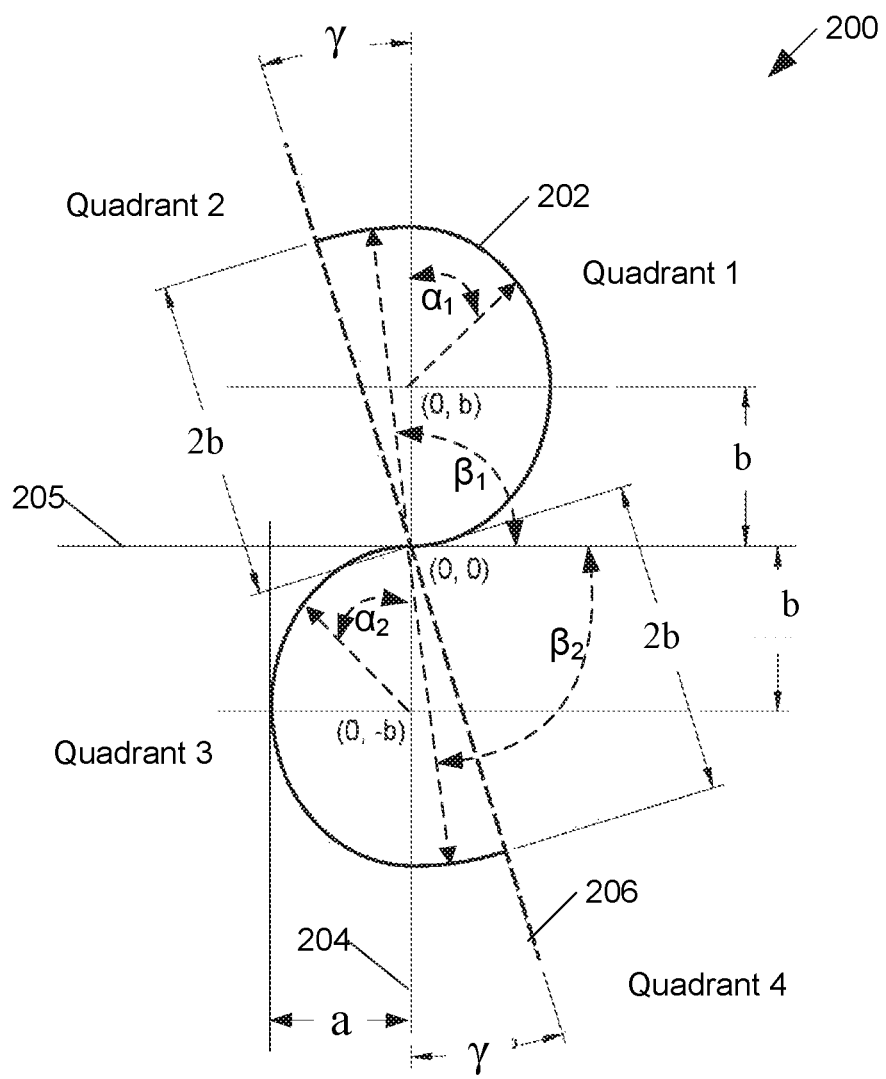
FIG. 5 is a profile of a cutting edge and parameter definitions of a particular embodiment

The cutting band 130 of an embodiment is curved according to the band profile 200 as illustrated in FIG. 5. Curved line 202 represents the cutting band 130. A line 206 from end to end of the cutting band curve 202 is offset by about 15 to 23 degrees relative to a Y axis 204 corresponding to an axis of longitudinal component 132 of the support element; the Y axis is perpendicular to an X axis 205 of the plot. In this embodiment, as viewed from above the cutting band 130, the cutting band extends along from 5 to 5.75 and preferably approximately 5.5 millimeters of the length of longitudinal component 132, and extends approximately one millimeter to each side of longitudinal component 132, and follows a profile as defined in the following equation group 1:

Along the X-Y Plane:
In the first quadrant:

$$x = a \cdot \cos(\alpha_1)$$

$$y = b \cdot \sin(\alpha_1) + b$$

and:
as the angle $\alpha_1$ is swept in a counterclockwise fashion from −90 degrees to +90 degrees with the center located at X=0, Y=b.
In the third quadrant:

$$x = -a \cdot \cos(\alpha_2)$$

$$y = b \cdot \sin(\alpha_2) - b$$

and:
as the angle $\alpha_2$ is swept in a counterclockwise fashion from 90 degrees to −90 degrees with the center located at X=0, Y=−b.
In the $2^{nd}$ quadrant:

$$x = 2b \cdot \cos(\beta_1)$$

$$y = 2b \cdot \sin(\beta_1)$$

where the angle $\beta_1$ is swept in a counterclockwise fashion from +90 degrees to 90+γ degrees with the center located at X=0, Y=0.
in the 4th quadrant:

$$x = 2b \cdot \cos(\beta_2)$$

$$y = 2b \cdot \sin(\beta_2)$$

where the angle $\beta_2$ is swept in a counterclockwise fashion from −90 degrees to −90+γ degrees with the center located at X=0, Y=0.
Where:
- x—the projection of a point of the locus described in the respective quadrant onto the X axis
- y—the projection of a point of the locus described in the respective quadrant on the Y axis
- a—½ of the transverse limit of the elliptical cutting profile, approximately 1 to 1.1 millimeter in an embodiment such that the cutting band extends approximately one millimeter to each side of the longitudinal component of the support structure
- b—½ of the longitudinal limit of the elliptical cutting profile, approximately 2.75 millimeters in an embodiment such that the cutting band extends approximately 5.5 millimeters along the longitudinal component of the support structure.
- α—sector angle of the elliptical locus of curvature
- β—sector angle of the circular locus of curvature
- γ—Limit angle, for an embodiment this angle is between 15 and 20 degrees.

For an embodiment the serrated cutting profile, the height of the cutting edge above the plane of the cut surface is defined by the following sinusoidal function:

$$h = h_o \cdot |(\sin(2\pi/s_o) \cdot s)|$$

where:
$h_o$—maximal height of the cutting edge above the cutting plane $$\frac{2\pi}{s_o} - \text{spatial frequency for the cutting profile}$$

and:

$$s_o = s_{max}/N$$

where
- $s_{max}$—the total path length of the elliptical or circular path locus
- N—number of teeth within the cutting path locus
- s—sector distance from the origin of the local s-z coordinate system and as measured along the curved cutting profile In alternative embodiments, alternative cutting tooth profiles representable as a sum of sines or cosines (Fourier series) are used.

In an embodiment, the cutting band 130 is made from a thin cross-section metal such as stainless steel, ceramic or hard plastic. The serrated shape of the cutting surface can be formed by micro injection molding, metal stamping, grinding or other metal forming processes.

The structural support longitudinal component 132 is incorporated into the instrument to provide axial and longitudinal stiffness to the band 130. The longitudinal component 132 is typically made from the same material as the cutting band. The support structure 104 is continuous with the longitudinal component 132, although it differs in cross sectional diameter. It provides a transition between the handle 102 and longitudinal component 132. Since it is undesirable to damage the central region of the cornea, support structure 104 has a curved profile to allow separation between the instrument and other intraocular tissues, support structure 104 is shaped to permit the supporting structure to pass through an incision at a side of a cornea of the eye while positioning the cutting band essentially flat on an anterior surface of the anterior capsule of the lens of the eye. The handle 102 allows the surgeon to manipulate the instrument. The handle will accommodate the proximal end of the support structure 104.

Figure 6:
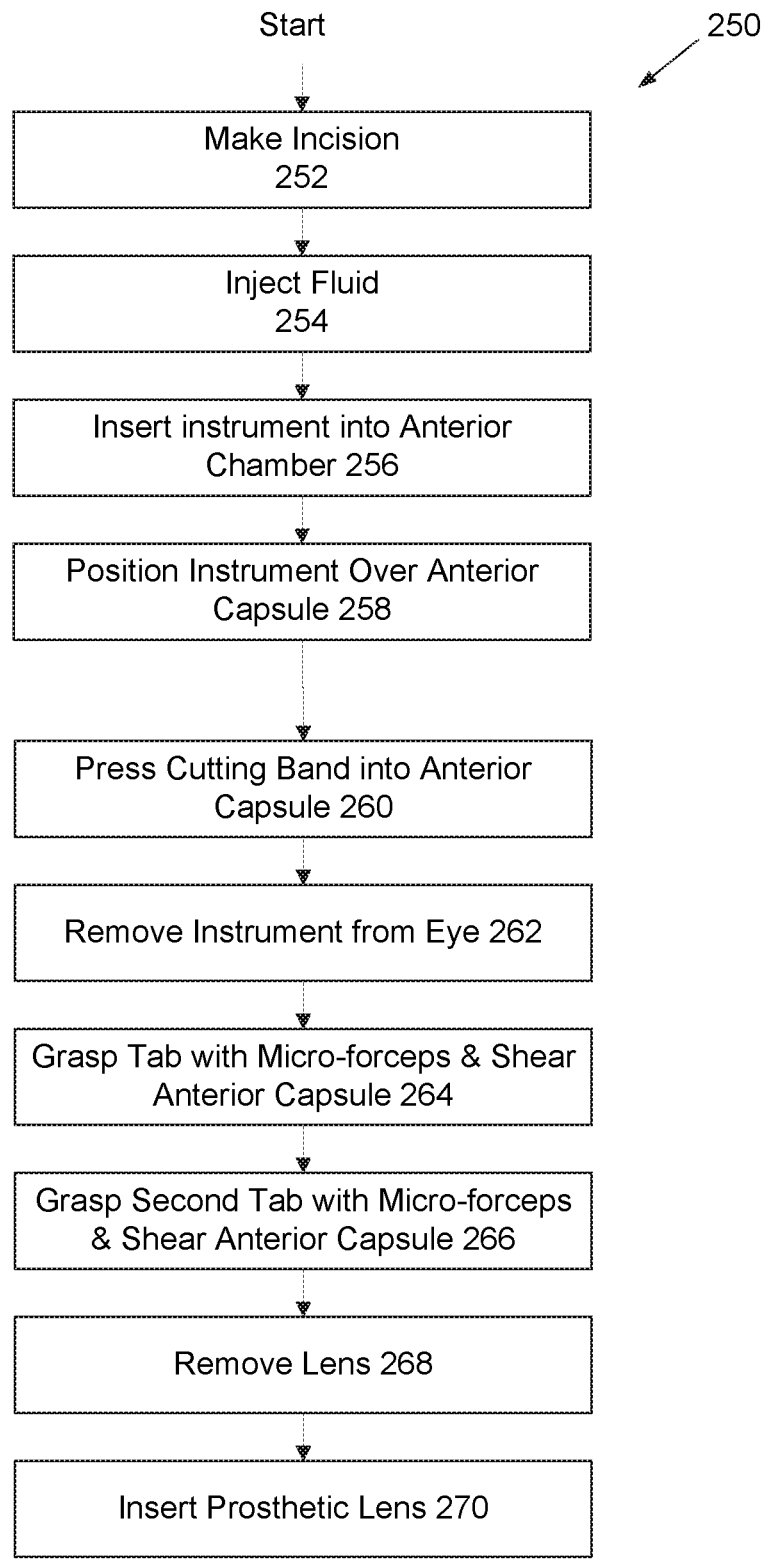
FIG. 6 is a flowchart of a surgical procedure using the instrument.

The flowchart of FIG. 6 and the following text describes how the instrument is used in a cataract extraction procedure 250. The surgeon makes 252 a corneal or scleral incision into the anterior chamber of the eye, the incision located at a side of the eye to avoid scarring or altering shape of the cornea, with a keratome of at least about 2.5 mm cutting width. An ophthalmic visco-elastic fluid is then be injected 254 into the eye to fill the anterior chamber. The instrument is then inserted 256 through the incision into the anterior chamber of the eye. The instrument is then centrally positioned 258 over the anterior capsule and gently displaced 260 towards the posterior pole of the eye. Because of the sharp serrated edge of the cutting band 130, only very gentle axially directed pressure is necessary to puncture the lens anterior capsule and shear the capsule with a precise curvilinear reverse-S (or S) shaped incision. The incision forms a first and a second tab, the first tab demarcated by the "top" of the reverse S shaped incision and the second tab demarcated by the "bottom" of the reverse S shaped incision, the shape of the tabs being defined by the curvature of the curvilinear cutting band. The instrument is then lifted above the anterior capsular plane and removed 262 from the anterior chamber of the eye. The reverse S shape incision created is in effect an open curvilinear capsulotomy with two tabs having precise limiting dimensions. In this example, 5.5 mm in greatest longitudinal extent and between 2 and 2.2 mm in greatest transverse extent. One tab is located proximal to the entrance wound, and the other, distal to the incision.

Figure 7:
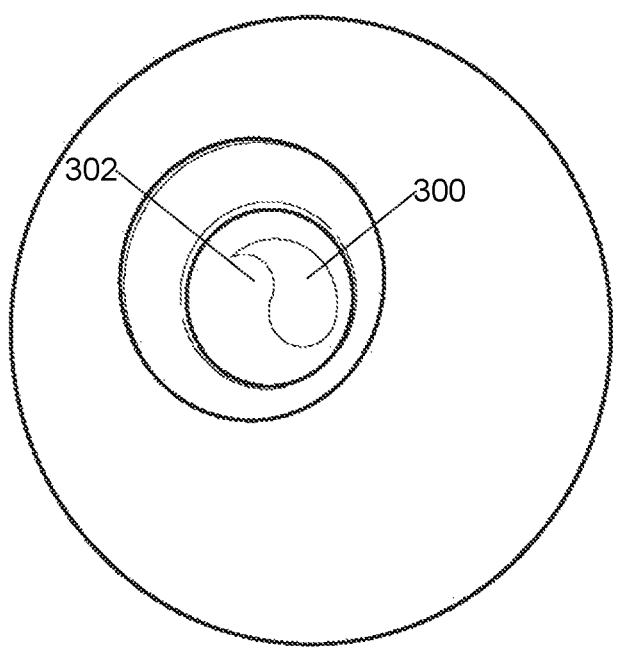
FIG. 7 is a perspective view of the initial capsulorhexis, after the distal tab is directed to shear the capsule and removed from the eye with micro forceps
Figure 8:
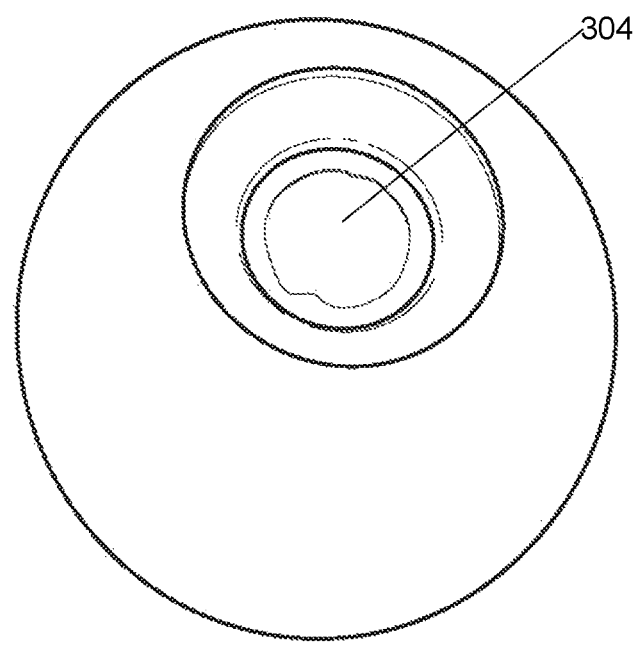
FIG. 8 is a view of the completed capsulorhexis, after both tabs are removed from the eye with micro forceps.

The proximal tab is then grasped with a fine micro forceps and sheared 264 off the anterior capsule in a counterclockwise direction away from the entrance wound. Ideally the surgeon will direct the tear so that it will follow a curvilinear path that approximates a circular arc and intersects the limiting distal boundary of the capsulotomy 300, as illustrated in FIG. 7. In a similar fashion, the distal tab 302 is then sheared 266 off in a direction that intersects the limiting proximal boundary of the capsulotomy. What is left is a closed continuous tear capsulorhexis 304. The exposed lens is then be removed 268 by the eye surgeons choice of nucleus disassembly and removal and replaced 270 with a prosthetic lens to complete the operation.

Figure 9:
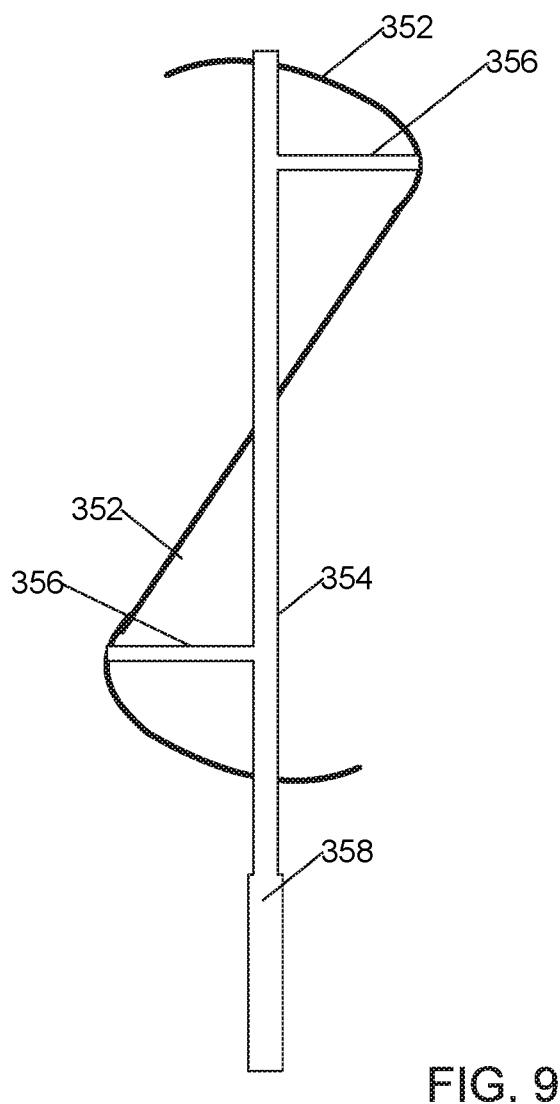
FIG. 9 is a top view of an alternative cutting head having a Z-shaped cutting band.

In an alternative embodiment, the reverse S shaped cutting edge is altered to have a squared or a double-triangular "Z" or reverse-"Z" shape as illustrated in FIG. 9, and performs similarly to create an incision in the anterior capsule with tabs that may be readily grasped and sheared. In the embodiment of FIG. 9, cutting band 352 is attached directly to longitudinal support component 354, and may also be attached to longitudinal support component 354 with transverse support components 356 and support structure 358, support structure 358 couples to a handle (not shown) as previously described. It should be noted that the tips of the Z are bent to direct any tears that may result in a direction around the desired capsulorhexis and away from the periphery of the anterior capsule, and the bends of the Z are rounded to discourage any tears from propagating from the bends.

Changes may be made in the above methods and systems without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present method and system, which, as a matter of language, might be said to fall therebetween.

The invention claimed is:

1. A method of performing cataract surgery comprising:
   making an incision in an eye;
   inserting a cutting tip of a stamping instrument into an anterior capsule of the eye, the cutting tip comprising a curvilinear cutting band and a support structure;
   aligning the cutting tip over the anterior capsule, and pressing the cutting tip into the anterior capsule to create a curvilinear incision in the capsule, the incision having a first and a second tab defined by curvature of the cutting band;
   removing the cutting tip of the instrument from the eye;
   grasping the first tab and tearing the anterior capsule to create an opening in the capsule and remove the tab from the eye;
   grasping the second tab and tearing the anterior capsule to enlarge the opening in the capsule and remove the tab from the eye, the opening forming a capsulorhexis;
   removing a natural lens of the eye from within the lens capsule; and
   inserting a prosthetic lens into the anterior capsule;
   wherein only a single stamping instrument having a cutting band with a single sharpened serrated edge is pressed into the anterior capsule.

2. The method of claim 1 wherein the curvilinear cutting band is curved into a shape selected from the group consisting of an "S" shape, a "Z" shape, a reverse "Z" shape, and a "reverse-S" shape.

3. A method of performing cataract surgery comprising:
   making an incision in an eye;
   inserting a cutting tip of an instrument into an anterior capsule of the eye, the cutting tip comprising a curvilinear cutting band and a support structure;
   aligning the cutting tip over the anterior capsule, and pressing the cutting tip into the anterior capsule to create a curvilinear incision in the capsule, the incision having a first and a second tab defined by curvature of the cutting band;
   removing the cutting tip of the instrument from the eye;
   grasping the first tab and tearing the anterior capsule to create an opening in the capsule and remove the tab from the eye;
   grasping the second tab and tearing the anterior capsule to enlarge the opening in the capsule and remove the tab from the eye, the opening forming a capsulorhexis;
   removing a natural lens of the eye from within the lens capsule; and
   inserting a prosthetic lens into the anterior capsule;
   wherein the curvilinear cutting band is curved into a shape selected from the group consisting of an "S" shape and a "reverse-S" shape.

4. The method of claim 3 wherein the cutting band has a serrated edge, and wherein in the step of pressing the cutting tip into the anterior capsule comprises pressing the serrated edge of the cutting band into the anterior capsule.

5. The method of claim 3 wherein the cutting band extends for between five and five and three-quarters millimeters from a first end of the shape to a second end of the shape.

6. A method of performing cataract surgery comprising:
   making an incision in an eye;

inserting a cutting tip of an instrument into an anterior capsule of the eye, the cutting tip comprising a curvilinear cutting band and a support structure;

aligning the cutting tip over the anterior capsule, and pressing the cutting tip into the anterior capsule to create a curvilinear incision in the capsule, the incision having a first and a second tab defined by curvature of the cutting band;

removing the cutting tip of the instrument from the eye;

grasping the first tab and tearing the anterior capsule to create an opening in the capsule and remove the tab from the eye;

grasping the second tab and tearing the anterior capsule to enlarge the opening in the capsule and remove the tab from the eye, the opening forming a capsulorhexis;

removing a natural lens of the eye from within the lens capsule; and inserting a prosthetic lens into the anterior capsule;

wherein the curvilinear cutting band is curved into a shape selected from the group consisting of an "Z" shape and a "reverse-Z" shape.

7. The method of claim 6 wherein the cutting band has a serrated edge, and wherein in the step of pressing the cutting tip into the anterior capsule comprises pressing the serrated edge of the cutting band into the anterior capsule.

8. The method of claim 6 wherein the cutting band extends for between five and five and three-quarters millimeters from a first end of the shape to a second end of the shape.

9. A method of performing cataract surgery comprising:
making an incision in an eye;

inserting a cutting tip of an instrument into an anterior capsule of the eye, the cutting tip comprising a curvilinear cutting band and a support structure;

aligning the cutting tip over the anterior capsule, and pressing the cutting tip into the anterior capsule to create a curvilinear incision in the capsule, the incision having a first and a second tab defined by curvature of the cutting band;

removing the cutting tip of the instrument from the eye;

grasping the first tab and tearing the anterior capsule to create an opening in the capsule and remove the tab from the eye;

grasping the second tab and tearing the anterior capsule to enlarge the opening in the capsule and remove the tab from the eye, the opening forming a capsulorhexis;

removing a natural lens of the eye from within the lens capsule; and inserting a prosthetic lens into the anterior capsule;

wherein, immediately prior to the step of grasping the first tab, the curvilinear incision in the anterior capsule is continuous between a first and a second end.

10. The method of claim 9 wherein the curvilinear cutting band is curved into a shape selected from the group consisting of an "S" shape, a "Z" shape, a reverse "Z" shape, and a "reverse-S" shape.

11. The method of claim 9 wherein the cutting band has a serrated edge, and wherein in the step of pressing the cutting tip into the anterior capsule comprises pressing the serrated edge of the cutting band into the anterior capsule.

12. The instrument method of claim 9 wherein the cutting band extends for between five and five and three-quarters millimeters from a first end of the cutting band to a second end of the cutting band.

13. The instrument method of claim 1 wherein the cutting band extends for between five and five and three-quarters millimeters from a first end of the cutting band to a second end of the cutting band.

* * * * *